United States Patent
Bachman et al.

[11] Patent Number: 6,056,710
[45] Date of Patent: May 2, 2000

[54] ORAL IRRIGATOR HOUSING

[75] Inventors: Timothy A. Bachman, Fort Collins; Tana Clare, Thornton, both of Colo.; Andrew Serbinski, Annandale, N.J.

[73] Assignee: Teledyne Industries, Inc., Fort Collins, Colo.

[21] Appl. No.: 09/217,973

[22] Filed: Dec. 18, 1998

[51] Int. Cl.[7] .................................................. A61H 9/00
[52] U.S. Cl. ................................................................ 601/162
[58] Field of Search ............................ 433/80; 601/162, 601/163, 164, 165

[56] References Cited

U.S. PATENT DOCUMENTS

| | | | |
|---|---|---|---|
| D. 246,667 | 12/1977 | Mackay et al. | 601/162 |
| 3,227,158 | 1/1966 | Mattingly . | |
| 3,420,228 | 1/1969 | Kalbfeld | 601/162 |
| 3,522,801 | 8/1970 | Robinson . | |
| 3,547,110 | 12/1970 | Balamuth . | |
| 3,636,947 | 1/1972 | Balamuth . | |
| 3,651,576 | 3/1972 | Massa . | |
| 3,809,977 | 5/1974 | Balamuth et al. . | |
| 4,060,870 | 12/1977 | Cannarella . | |
| 4,075,761 | 2/1978 | Behne et al. . | |
| 4,108,178 | 8/1978 | Betush . | |
| 4,144,646 | 3/1979 | Takemoto et al. . | |
| 4,182,038 | 1/1980 | Fleer | 433/85 |
| 4,215,476 | 8/1980 | Armstrong | 433/80 |
| 4,219,618 | 8/1980 | Leonard | 433/80 |
| 4,227,878 | 10/1980 | Löhn | 433/80 |
| 4,229,634 | 10/1980 | Hickman et al. | 200/302 |
| 4,236,889 | 12/1980 | Wright | 433/86 |
| 4,249,899 | 2/1981 | Davis | 433/80 |
| 4,266,934 | 5/1981 | Pernot | 433/85 |
| 4,276,023 | 6/1981 | Phillips et al. | 433/85 |
| 4,302,186 | 11/1981 | Cammack et al. | 433/80 |
| 4,331,422 | 5/1982 | Heyman | 433/125 |
| 4,340,365 | 7/1982 | Pisanu | 433/80 |
| 4,340,368 | 7/1982 | Lococo | 433/99 |
| 4,363,626 | 12/1982 | Schmidt et al. | 433/85 |
| 4,365,376 | 12/1982 | Oda et al. | 15/22.1 |
| 4,382,786 | 5/1983 | Löhn | 433/85 |
| 4,412,823 | 11/1983 | Sakai et al. | 433/80 |
| 4,452,238 | 6/1984 | Kerr | 601/162 |
| 4,517,962 | 5/1985 | Heckele | 433/80 |
| 4,531,912 | 7/1985 | Schuss et al. | 433/80 |
| 4,531,913 | 7/1985 | Taguchi | 433/80 |
| 4,602,906 | 7/1986 | Grünenfelder | 433/80 |
| 4,619,612 | 10/1986 | Weber et al. | 433/80 |
| 4,629,425 | 12/1986 | Detsch | 433/80 |
| 4,648,838 | 3/1987 | Schlachter | 433/80 |
| 4,655,198 | 4/1987 | Hommann | 433/80 |
| 4,669,453 | 6/1987 | Atkinson et al. | 433/80 |
| 4,672,953 | 6/1987 | DiVito | 433/80 |
| 4,787,847 | 11/1988 | Martin et al. | 433/119 |
| 4,803,974 | 2/1989 | Powell | 222/79 |

(List continued on next page.)

OTHER PUBLICATIONS

WOOG® Products at a Glance Brochure, Home Dental Care System, WOOG ORAJET, at least as early as Dec. 18, 1998.

*Primary Examiner*—John J. Wilson
*Attorney, Agent, or Firm*—Holland & Hart LLP

[57] ABSTRACT

A housing for an oral irrigator having a hand piece includes a base unit having an upper and lower portion, the lower portion engageable with a support surface and having an upper surface defining a recess for receiving the hand piece, and the lower portion defining a peripheral shoulder. The upper portion extends upwardly from the lower portion and defines a top surface, the top surface defining a port and a key structure, the upper portion being positioned inside the peripheral shoulder. A reservoir has a bottom surface defining an aperture and sidewalls extending upwardly from the bottom surface to define a cavity having a peripheral rim, the sidewalls in part defining an indentation extending from the bottom surface up to a top end adjacent the peripheral rim at a position interior to the peripheral rim. A top wall extends from the top end of the indentation to the peripheral rim, the top wall forming an overhang. The bottom of the reservoir also defines a recess to receive the key formed on the top of the base unit for positional orientation during placement of the reservoir on the base unit.

2 Claims, 5 Drawing Sheets

U.S. PATENT DOCUMENTS

| | | | |
|---|---|---|---|
| 4,804,364 | 2/1989 | Dieras et al. | 433/86 |
| 4,818,229 | 4/1989 | Vasile | 433/86 |
| 4,820,152 | 4/1989 | Warrin et al. | 433/86 |
| 4,826,431 | 5/1989 | Fujimura et al. | 433/80 |
| 4,832,683 | 5/1989 | Idemoto et al. | 433/86 |
| 4,854,869 | 8/1989 | Lawhorn | 433/80 |
| 4,886,452 | 12/1989 | Löhn | 433/80 |
| 4,902,225 | 2/1990 | Löhn | 433/80 |
| 4,903,687 | 2/1990 | Lih-Sheng . | |
| 4,906,187 | 3/1990 | Amadera | 433/80 |
| 4,928,675 | 5/1990 | Thornton | 433/80 |
| 4,950,159 | 8/1990 | Hansen | 433/80 |
| 4,961,698 | 10/1990 | Vlock | 433/86 |
| 4,973,247 | 11/1990 | Varnes et al. | 433/85 |
| 4,975,054 | 12/1990 | Esrock | 433/80 |
| 4,979,503 | 12/1990 | Chernack | 433/88 |
| 4,989,590 | 2/1991 | Baum et al. . | |
| 4,998,880 | 3/1991 | Nerli | 433/80 |
| 5,013,241 | 5/1991 | von Gutfeld et al. | 433/86 |
| 5,027,798 | 7/1991 | Primiano . | |
| 5,033,961 | 7/1991 | Kankler et al. . | |
| 5,082,443 | 1/1992 | Löhn | 433/80 |
| 5,086,756 | 2/1992 | Powell . | |
| 5,095,893 | 3/1992 | Rawden, Jr. . | |
| 5,125,835 | 6/1992 | Young | 433/80 |
| 5,142,723 | 9/1992 | Lustig et al. | 15/22.1 |
| 5,199,871 | 4/1993 | Young | 433/80 |
| 5,204,004 | 4/1993 | Johnston et al. | 433/80 |
| 5,218,956 | 6/1993 | Handler et al. . | |
| 5,220,914 | 6/1993 | Thompson . | |
| 5,235,968 | 8/1993 | Woog | 433/80 |
| 5,246,367 | 9/1993 | Ito et al. | 433/80 |
| 5,252,064 | 10/1993 | Baum et al. | 433/80 |
| 5,257,933 | 11/1993 | Jousson | 433/80 |
| 5,281,137 | 1/1994 | Jousson | 433/80 |
| 5,286,201 | 2/1994 | Yu | 433/80 |
| 5,321,865 | 6/1994 | Kaeser | 15/22.1 |
| 5,344,317 | 9/1994 | Pächer et al. | 433/80 |
| 5,378,149 | 1/1995 | Stropko | 433/80 |
| 5,399,089 | 3/1995 | Eichman et al. | 433/80 |
| 5,456,672 | 10/1995 | Diederich et al. | 433/80 |
| 5,468,148 | 11/1995 | Ricks | 433/80 |
| 5,470,305 | 11/1995 | Arnett et al. | 433/80 |
| 5,474,450 | 12/1995 | Chronister | 433/80 |
| 5,484,281 | 1/1996 | Renow et al. | 433/80 |
| 5,547,374 | 8/1996 | Coleman | 433/85 |
| 5,554,025 | 9/1996 | Kinsel | 433/80 |
| 5,616,028 | 4/1997 | Häfele et al. | 433/80 |
| 5,636,987 | 6/1997 | Serfaty | 433/80 |
| 5,640,735 | 6/1997 | Manning | 15/29 |
| 5,697,784 | 12/1997 | Häfele et al. | 433/85 |
| 5,709,545 | 1/1998 | Johnston et al. | 433/80 |

ORAL IRRIGATOR HOUSING

This application is related to co-pending application entitled "Oral Irrigator Handle Assembly Having a Pressure Control Valve and Stop Valve Assembly," Ser. No. 09/217,972, filed concurrently herewith, and assigned to the assignee of this application, the disclosure of which is hereby incorporated by reference in its entirety.

FIELD OF THE INVENTION

This invention relates to oral irrigator housings, and more particularly relates to oral irrigator housings that are keyed to maintain proper orientation between the base and reservoir, and provide protection of the hand piece.

BACKGROUND OF THE INVENTION

Oral irrigators are very popular dental hygiene apparatus for use in maintaining healthy gums. Typically, however, oral irrigators are relatively bulky and thus difficult set down for use. Since oral irrigators are often used in bathrooms, and typically bathrooms have little or no counter top space, their size makes them sometimes hard to use. Their size also makes oral irrigators difficult to store when not in use.

Where an oral irrigator includes a removable reservoir for easy filling, these reservoirs are difficult to reposition properly on the base since the reservoir and the base have to be properly engaged to insure the fluid communication from the reservoir to the base is fluid-tight and does not leak. It is sometimes very difficult to reposition the reservoir without any guide or positional guidance.

Further, when the hand piece is stored in the base it is often subject to inadvertent contact which can dislodge or damage the hand piece. Typical oral irrigators allow the hand piece to be stored upright next to the reservoir, but in this position the hand piece is exposed from all but one side to inadvertent and potentially damaging contact by the user.

What is needed in the art is an oral irrigator housing that has a positional orientation structure to make attachment of the separable reservoir to the base more easily accomplished. In addition, an oral irrigator housing that forms a protective envelope around the hand piece while stored upright on the base is needed.

SUMMARY OF THE INVENTION

The oral irrigator housing of the present invention was developed with the shortcomings of the available housings described above in mind. The present invention provides an oral irrigator with an improved reservoir placement guide to facilitate easier and more accurate positioning of the reservoir on the top of the base unit in the upright position. In addition, the reservoir in the upright position acts to protect the stored hand piece by surrounding the hand piece in an indentation in the reservoir. The reservoir is also useable as a cover to protect the handle and jet tips, and to allow the oral irrigator to be stored more easily.

In more detail, a housing for an oral irrigator having a hand piece includes a base unit having an upper and lower portion, the lower portion engageable with a support surface and having an upper surface defining a recess for receiving the hand piece, and the lower portion defining a peripheral shoulder. The upper portion extends upwardly from the lower portion and defines a top surface, the top surface defining a port, the upper portion being positioned inside the peripheral shoulder. A reservoir has a bottom surface defining an aperture and sidewalls extending upwardly from the bottom surface to define a cavity having a peripheral rim, the sidewalls in part defining an indentation extending from the bottom surface up to a top end adjacent the peripheral rim at a position interior to the peripheral rim. A top wall extends from the top end of the indentation to the peripheral rim, the top wall forming an overhang.

The reservoir is positionable on the base unit such that the peripheral rim engages the peripheral shoulder on the housing unit to encompass the upper portion of the motor housing unit in the cavity. The reservoir is also positionable on the base unit such that the bottom surface of the reservoir rests on the top surface of the upper portion with the port and the aperture in alignment and sealingly engaged. The indentation is oriented with the recess, wherein the hand piece is received in the indentation and covered by the top wall.

In addition, the housing can further include a key extending upwardly from the top surface of the base unit, with the bottom surface of the reservoir defining a recess having a complimentary shape to the key. The key is received in the recess when the reservoir is positioned on the base unit such that the bottom surface of the reservoir rests on the top surface of the upper portion with the port and the aperture in alignment and sealingly engaged.

A more complete appreciation of the present invention and its scope can be obtained from understanding the accompanying drawings, which are briefly summarized below, the following detailed description of the presently preferred embodiments of the invention, and the appended claims.

DETAILED DESCRIPTION OF THE PREFERRED EMBODIMENT

Figure 1:
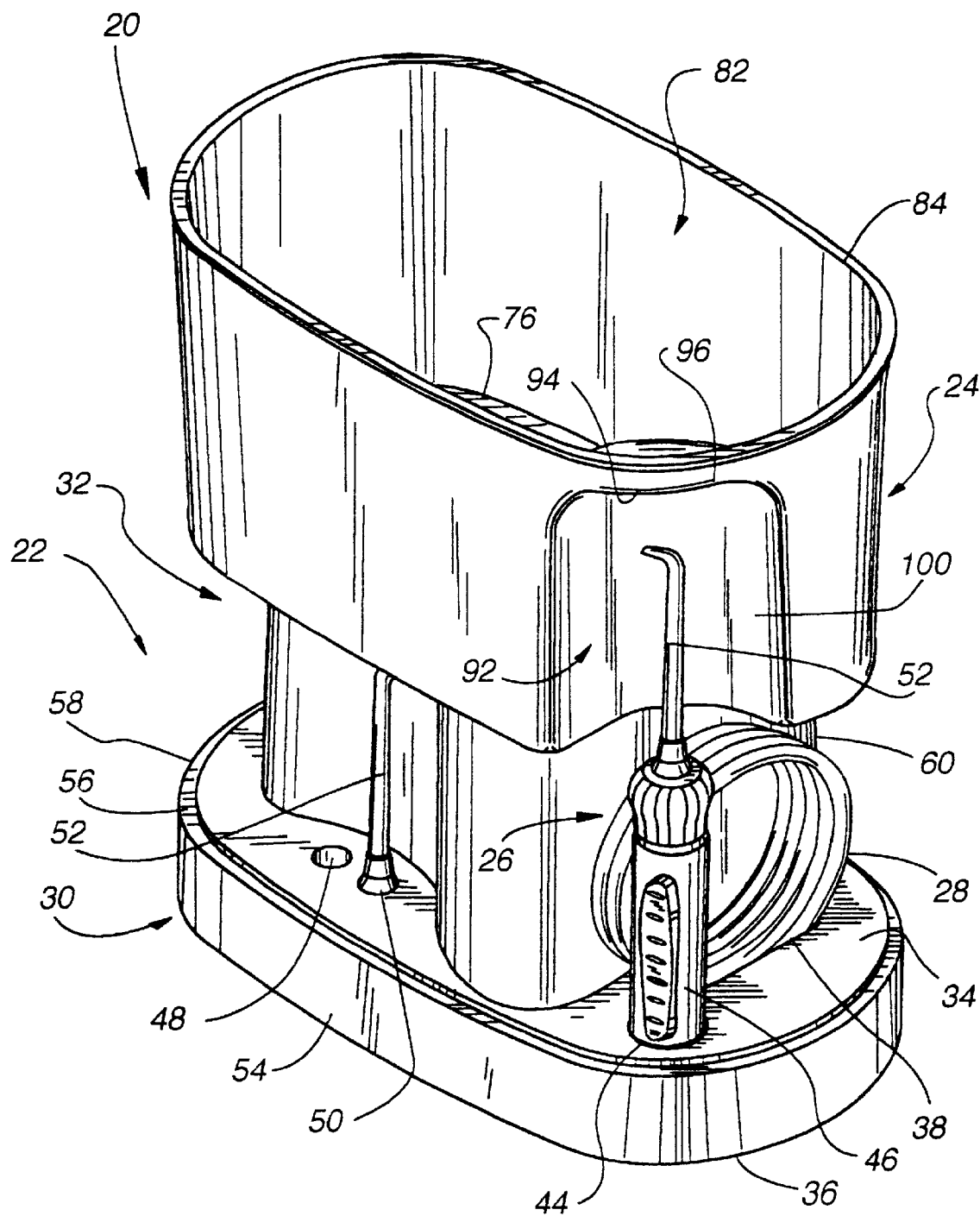
FIG. 1 is a perspective view of the oral irrigator housing incorporating the present invention showing the reservoir in the upright position on the base unit, and the hand piece positioned in the indentation formed in the reservoir.

The oral irrigator housing 20 incorporating the present invention is shown in FIG. 1. The housing 20 includes a base unit 22 and a reservoir 24 for either holding water to supply the base unit 22 or covering the base unit 22. A hand piece 26 is attached by a tube 28 to the base unit 22, and is used to direct a pulsated water stream. The oral irrigator is used as a part of proper dental hygiene practice.

Figure 3:
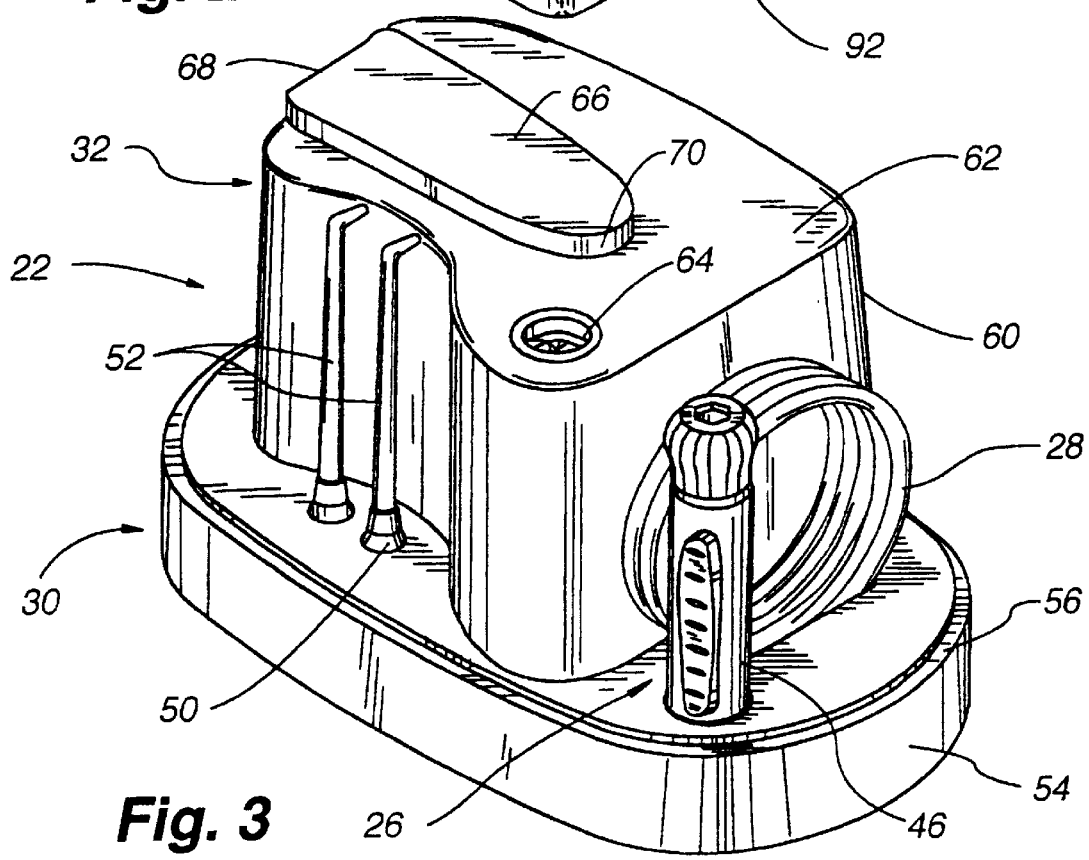
Figure 5:
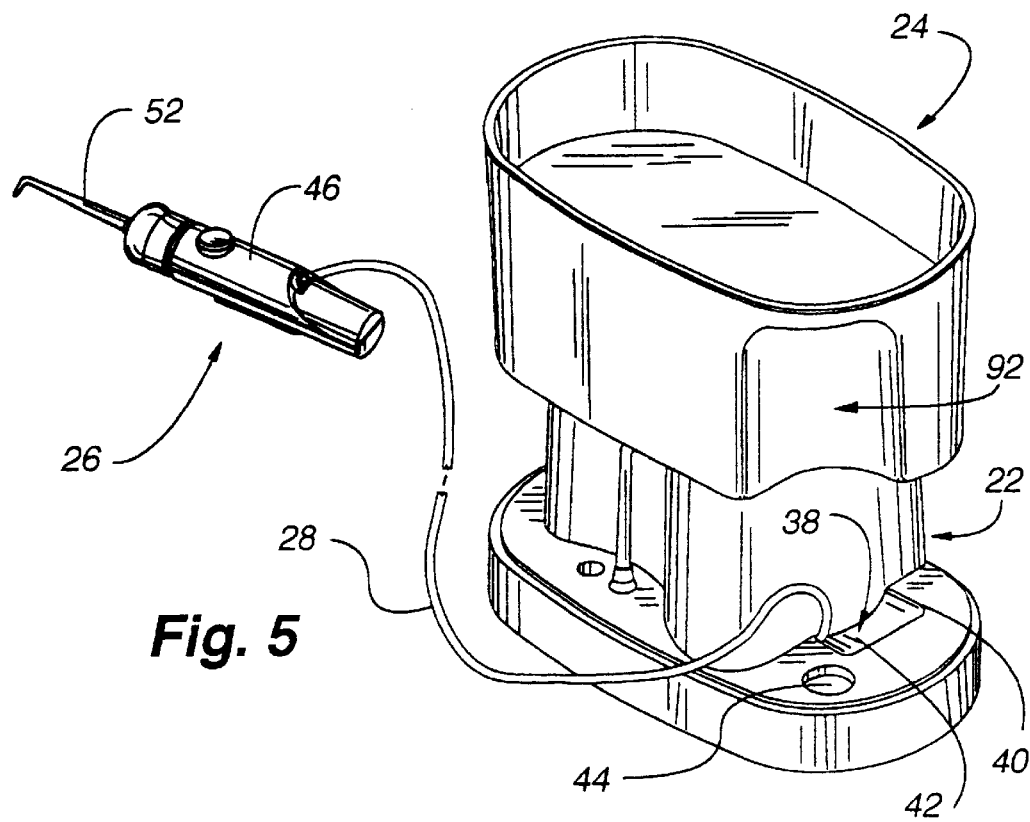
FIG. 5 is a perspective view of the oral irrigator showing the hand piece removed from its storage recess on the base unit.

As best shown in FIGS. 1 and 3, the base unit 22 has a lower portion 30 and an upper portion 32, with the upper portion 32 extending upwardly from the lower portion 30 and leaving an exposed upper surface 34. The lower portion 30 has a bottom 36 for resting on a support surface, such as a table, sink or dresser. The upper surface 34 defines a recess 38 (see FIG. 5) having a rectangular perimeter 40 and a curved bottom 42 for storing the tube 28 in coiled form. In addition, the upper surface 34 includes a substantially circular recess 44 for receiving the handle 46 of the hand piece 26 and holding it in an upright position adjacent to the upper portion 32 of the base unit 22. The upper surface 34 also defines at least one recess 48 for receiving the base 50 of the jet tip portion 52 of the hand piece 26. The lower portion 30 of the base unit 22 also includes a lower skirt 54 which defines a continuous peripheral shoulder 56 at its top edge 58, at the intersection of the peripheral skirt 54 and the upper surface 34 of the lower portion 30.

The upper portion 32 of the base unit 22 extends upwardly from the upper surface 34 of the lower portion 30 and is contained within the peripheral shoulder 56. The upper portion 32 has curved, substantially vertical side walls 60 and a top surface 62. The top surface 62 is relatively planar, and defines a portal 64 formed therein. A keyed protrusion 66 is formed in the top surface 62 and extends from one end of the top surface 62 toward the opposite end along the length dimension of the upper portion 32. The keyed protrusion 66 has a first flat wide end 68 adjacent the end of the top surface 62, and a second curved narrow end 70 opposite the first end 68. The width between the first and second ends preferably widens slightly in the middle and then narrows to the curved second end tip 70.

The base unit 22 houses a motor and pump for providing a pulsated stream of water to the hand piece 26. A suitable pump and motor is disclosed in U.S. Pat. No. 4,989,590, entitled "Irrigation Appliance", issued Feb. 5, 1991, and assigned to the assignee of the present application, which is hereby incorporated by reference in its entirety, or in U.S. Pat. No. 5,399,089, entitled "Oral Hygiene Appliance", issued Mar. 21, 1995, and assigned to the assignee of the present application, which is also incorporated by reference herein in its entirety. The pump receives water from the fluid stored in the reservoir 24, as described in more detail below. The motor is powered by line voltage, connected through an outlet cord 72 and plug 74 to a standard electric outlet.

The tube 28 is attached to the output of the pump and carries the pulsed fluid to the hand piece 26. The hand piece 26 includes a handle 46 and a separable jet tip 52, and is used to direct the pulsed fluid in the desired direction. A suitable hand piece 26 is disclosed in U.S. Pat. No. 5,399,089, entitled "Oral Hygiene Appliance", issued Mar. 21, 1995, and assigned to the assignee of the present application, or in related application "Oral Irrigator Handle Assembly Having a Pressure Control Valve and Stop Valve Assembly," Attorney Docket Number 16284.830026.000, Serial Number XX/XXX,XXX, filed concurrently herewith and assigned to the assignee in this application, both incorporated by reference herein in their entirety. The hand piece 26 can be stored in the base unit 22 in the recess 44 formed in the upper surface 34 of the lower portion 30. The hand piece 26 is stored in an upright orientation adjacent to the upper portion 32 of the base unit 22.

Figure 2:
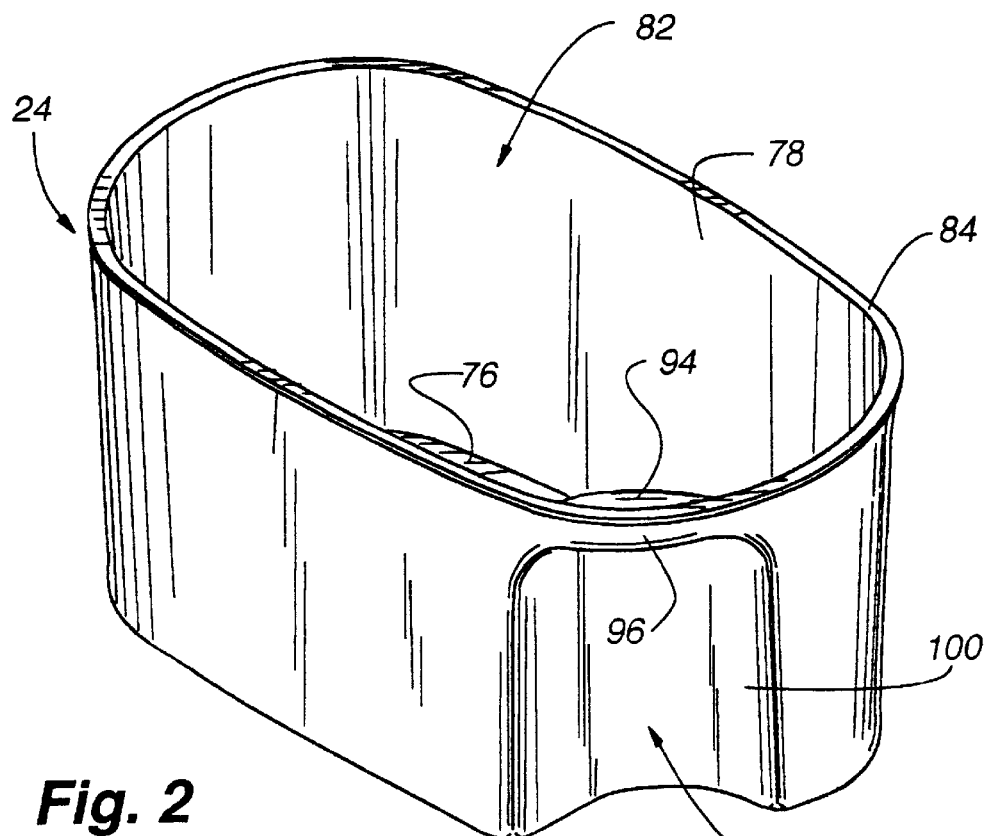
FIGS. 2–3 are together an exploded perspective view of the oral irrigator housing of FIG. 1.
Figure 4:
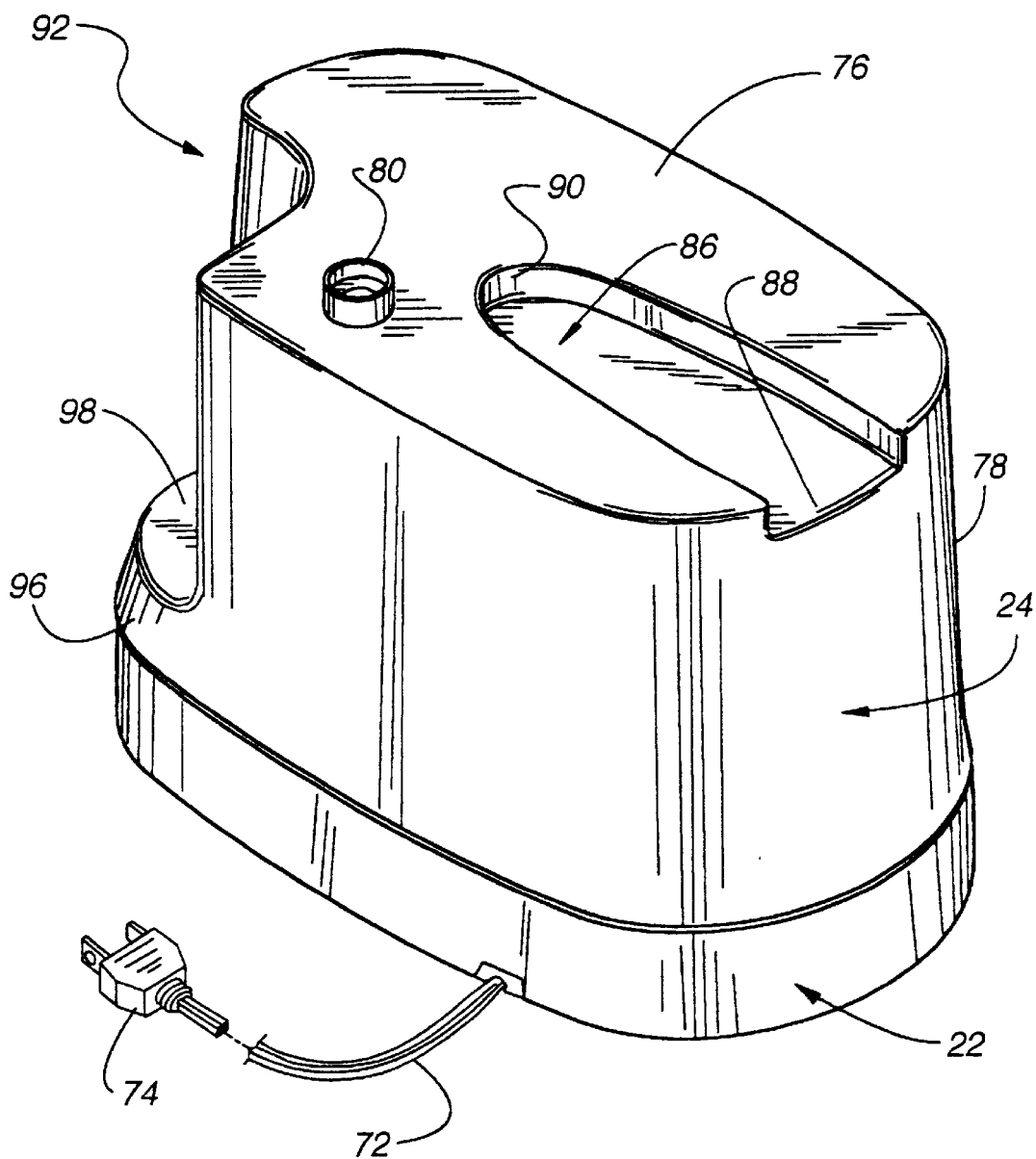
FIG. 4 is a perspective view of the oral irrigator housing of FIG. 1 with the reservoir in the cover position.

As best shown in FIGS. 1, 2 and 4, the reservoir 24 has a bottom surface 76 defining an aperture 80, and side walls 78 extending upwardly from the bottom surface 76. The combination of the bottom surface 76 and the side walls 78 form a cavity 82 having a peripheral rim 84 defining an opening. The bottom surface 76 of the reservoir 24 also defines a recess 86 having the complimentary shape to the key protrusion 66 formed on the top surface 34 of the upper portion 32 of the base unit 22. The recess 86 extends from one end of the bottom surface 76 toward the opposite end along the length dimension of the reservoir 24. The recess 86 is formed at the intersection of the bottom surface 76 and the side wall 78, and thus forms a recess in the side wall 78. The keyed recess 86 has a first flat wide end 88 adjacent the end of the bottom surface 76, and a second curved narrow end 90 opposite the first end 88. The width between the first and second ends preferably widens slightly in the middle and then narrows to the curved second end tip 90. The reservoir 24 is preferably made of plastic, such as ABS or high-impact poly-styrene.

The side walls 78 also define, at a corner of the reservoir 24, an indentation 92 extending upwardly from the bottom surface 76 to a top end 94 adjacent the peripheral rim 84. The indented area 92 extends inwardly from the peripheral rim 84. A top wall 96 extends from the top end 94 of the indentation 92 to the peripheral rim 84, and forms an overhang 98. The walls 100 of the indentation are preferably at right angles to one another, with a rounded intersection between the walls. The walls 100 of the indentation intersect the top wall 96 in a rounded corner.

The reservoir 24 is positionable on the base unit 22 in two different orientations, upright and as a cover, each with its own benefits. In the upright position, the bottom surface 76 of the reservoir 24 contacts the upper surface 34 of the upper portion 32 of the base 22. In the upright position, the reservoir 24 can hold water to supply to the pump for passage through the hand piece 26 as desired. To supply water to the pump, the aperture 80 formed in the bottom surface 76 of the reservoir 24 orients with and sealingly engages the portal 64 formed in the top surface 62 of the upper portion 32 of the base unit 22. The structure allowing the aperture to sealingly engage the portal 64 is any known or available structure, such as that disclosed in U.S. Pat. No. 5,399,089 referenced above.

The reservoir 24 is properly positioned on the base unit 22 by the positioning of the key 66 on the top surface 62 of the upper portion 32 of the base unit 22 in the complimentarily-shaped recess 86 formed in the bottom surface 76 of the reservoir 24. The elongated key 66 can enter the end of the recess 86 as the reservoir 24 is moved lengthwise over the base 22 to where the tip 70 of the key 66 engages the tip 90 of the recess 86. At this point the entire length of the key 66 is positioned within the recess 86. The sidewalls of the key 66 engage the sidewalls of the recess 86 to help maintain the proper lateral positioning of the reservoir 24 on the top surface 62 of the base unit 22. When the tip 70 of the key 66 engages the tip 90 of the recess 86, the longitudinal positioning and lateral positioning of the reservoir 24 is proper, and the aperture 80 and portal 64 are aligned for sealing engagement. This guided engagement is easily initiated by the user inserting the tip 70 of the key 66 into the open end 88 of the recess 86, and moving the reservoir 24 longitudinally along the top of the base unit 22 until the tip 70 of the key 66 and the tip 90 of the recess 86 engage.

This keyed orientation of the reservoir 24 and base unit 22 is important for several reasons. One important reason is that the reservoir 24 is typically mounted on the base 22 after being filled with water. The key structure acts as a guide so the user does not have to guess the proper centered position of the reservoir 24 on the base unit 22, and also does not have to estimate where the aperture 80 is properly oriented with the portal 64.

After the reservoir 24 has been properly positioned, the user actuates the motor and pump by the on-off slide switch on the base unit 22. The pump draws water out of the reservoir 24 and pumps it through the hand piece 26 until the reservoir 24 is empty.

Figure 6:
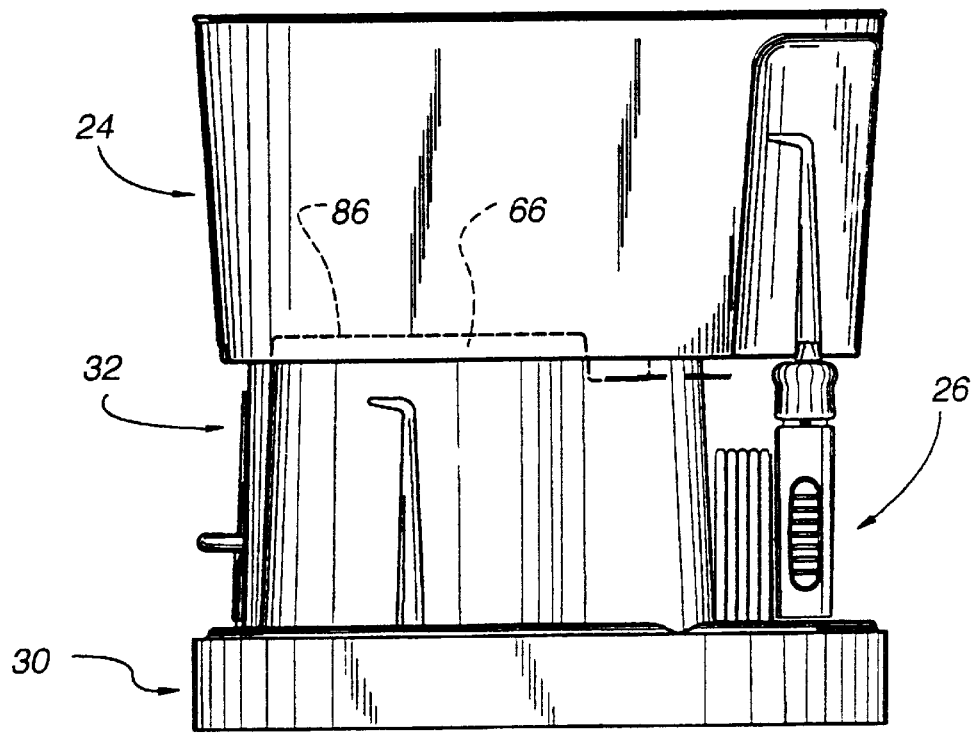
FIG. 6 is a side view of the oral irrigator with the reservoir in the upright position, and the hand piece positioned in the indentation.

Another benefit of the placement of the reservoir 24 in the upright position on the base unit 22 is that it protects the hand piece 26 stored in the upright position in the base unit 22. The hand piece 26 extends upwardly, as shown in FIGS. 1 and 6 at a position to extend into and be received by the indentation 92 in the reservoir 24. The top wall 96 extends over the hand piece 26, and two adjacent sidewalls 100 of the indentation 92 protect the hand piece from incidental vertical or lateral contact by the user. This is a distinct advantage over other oral irrigators, where the hand piece is left exposed to incidental contact and possible damage.

Once empty and the user has completed his or her use of the oral irrigator, the reservoir 24 can be disengaged from the top of the base unit 22 and inverted to be placed over the base unit 22, as shown in FIG. 4. In this cover position, the jet tip 52 of the hand piece 26 must be removed and stored in its particular storage location in the lower portion 30 of the base unit 22, but the handle 46 of the hand piece 26 can remain in its particular recess 44. The peripheral rim 84 of the reservoir 24 engages the peripheral shoulder 56 on the lower portion 30 of the base unit 22 to orient the reservoir 24 and hold it in place. The reservoir 24 in the cover position allows the oral irrigator to have a reduced size for storage, and helps keep the handle 46 and jet tips 52 from being dislodged, lost or damaged.

Figure 8:
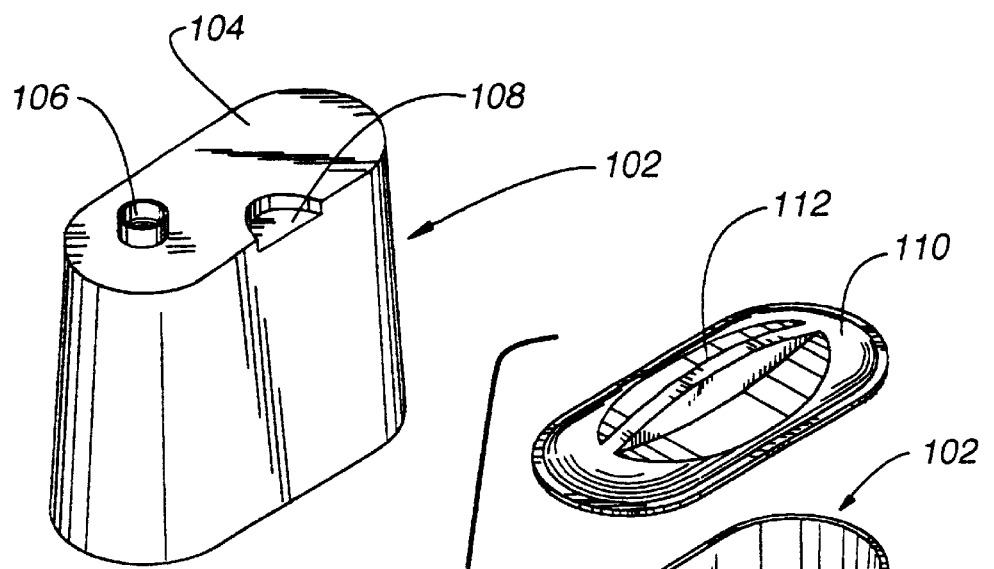
FIG. 8 is a bottom perspective view of the medicament reservoir.
Figure 7:
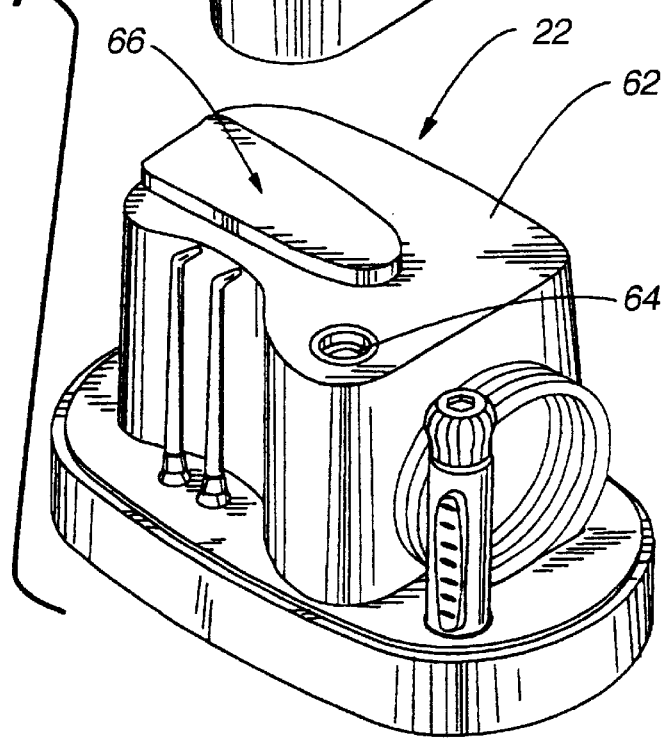
FIG. 7 is an exploded view of the oral irrigator housing showing a medicament reservoir and cover.

FIGS. 7 and 8 show an alternative embodiment of the reservoir 24 for use on the base unit 22. This alternative reservoir 102 is smaller, for use with smaller volumes of liquid, such as when medicament is to be used in the oral irrigator. The bottom surface 104 of the medicament reservoir 102 defines an aperture 106 identical to the aperture above. The bottom surface 104 of the medicament reservoir 102 also forms a recess 108 in the same spatial orientation to the aperture as that described above. The recess 108 on the bottom surface 104 of the medicament reservoir 102 is relatively short in length and receives the tip 70 and a short length of the key 66 formed on the top of the base unit 22. The majority of the length of the key 66 extends outside the recess. Nonetheless, the recess 108 works in combination with the key 66 as a guide to properly position the medicament reservoir 102 on the top surface 62 of the base unit 22 for proper orientation of the aperture 106 with the portal 64. The medicament reservoir 102 includes a top cover 110 having a ridge-type handle 112 extending longitudinally along the top cover 110. The top cover 110 is used to close the open end of the medicament reservoir if desired.

In operation, the present invention provides an oral irrigator with an improved reservoir placement guide to facilitate easier and more accurate positioning of the reservoir on the top of the base unit 22 in the upright position. In addition, the reservoir in the upright position acts to protect the stored hand piece by surrounding the hand piece in an indentation in the reservoir. The reservoir is also useable as a cover to protect the handle and jet tips, and to allow the oral irrigator to be stored more easily.

A presently preferred embodiment of the present invention and many of its improvements have been described with a degree of particularity. It should be understood that this description has been made by way of example, and that the invention is defined by the scope of the following claims.

What is claimed is:

1. A housing for an oral irrigator having a hand piece, said housing comprising:

a base unit having an upper and lower portion, said lower portion engageable with a support surface and having an upper surface defining a recess for receiving the hand piece and defining a peripheral shoulder, said upper portion extending upwardly from said lower portion and defining a top surface, said top surface defining a port, said upper portion positioned inside said peripheral shoulder;

a reservoir having a bottom surface defining an aperture and sidewalls extending upwardly from said bottom surface defining a cavity having a peripheral rim, said sidewalls in part defining an indentation extending from said bottom surface up to a top end adjacent said peripheral rim at a position interior to said peripheral rim, and a top wall extending from said top end of said indentation to said peripheral rim, said top wall forming an overhang;

said reservoir positionable on said base unit such that said peripheral rim engages said peripheral shoulder on said housing unit to encompass said upper portion of said motor housing unit in said cavity, and positionable on said base unit such that said bottom surface of said reservoir rests on said top surface of said upper portion with said port and said aperture in alignment and sealingly engaged, and said indentation being oriented with said recess, wherein the hand piece is received in said indentation and covered by said top wall.

2. A housing as defined in claim 1, wherein:

said top surface of said upper portion of said base defining a key extending upwardly from said top surface;

said bottom surface of said reservoir defining a recess having a complimentary shape to said key;

said key being received in said recess when said reservoir is positioned on said base unit such that said bottom surface of said reservoir rests on said top surface of said upper portion with said port and said aperture in alignment and sealingly engaged.

* * * * *